US009710608B2

(12) United States Patent
Mikhail

(10) Patent No.: US 9,710,608 B2
(45) Date of Patent: Jul. 18, 2017

(54) PILL BOTTLE LID INCORPORATING AUDIBLE MESSAGING DEVICE, AND PAIRING THEREOF WITH EXTERNAL DEVICES FOR DOSAGE REMINDER AND CONFLICT CHECKING PURPOSES

(71) Applicant: Tamer S. M. Mikhail, Unionville (CA)

(72) Inventor: Tamer S. M. Mikhail, Unionville (CA)

( * ) Notice: Subject to any disclaimer, the term of this patent is extended or adjusted under 35 U.S.C. 154(b) by 0 days.

(21) Appl. No.: 14/737,027

(22) Filed: Jun. 11, 2015

(65) Prior Publication Data
US 2015/0360834 A1  Dec. 17, 2015

Related U.S. Application Data

(60) Provisional application No. 62/010,537, filed on Jun. 11, 2014.

(51) Int. Cl.
| | | |
|---|---|---|
| *G07F 11/00* | (2006.01) | |
| *G06F 19/00* | (2011.01) | |
| *A61J 1/14* | (2006.01) | |
| *B65D 43/16* | (2006.01) | |
| *B65D 51/24* | (2006.01) | |
| *A61J 1/03* | (2006.01) | |

(52) U.S. Cl.
CPC ........ *G06F 19/3462* (2013.01); *A61J 1/1425* (2015.05); *B65D 43/163* (2013.01); *B65D 51/248* (2013.01); *A61J 1/03* (2013.01); *A61J 2205/70* (2013.01)

(58) Field of Classification Search
CPC ...................................... B65D 51/24
USPC ..... 340/539.12, 309.16, 309.2, 309.3, 309.4, 340/309.7, 309.8, 384.5, 384.71; 704/274; 368/109, 110
See application file for complete search history.

(56) References Cited

U.S. PATENT DOCUMENTS

| | | | | |
|---|---|---|---|---|
| 5,011,032 A | * | 4/1991 | Rollman ................ | A61J 7/04 116/321 |
| 5,625,334 A | * | 4/1997 | Compton ............... | A61J 7/0472 116/308 |
| 6,158,613 A | * | 12/2000 | Novosel et al. ................... | 221/3 |
| 6,324,123 B1 | * | 11/2001 | Durso ................... | A61J 7/0481 221/15 |
| 7,719,927 B1 | * | 5/2010 | Robinson ............... | A61J 7/0445 215/230 |
| 2008/0210755 A1 | * | 9/2008 | Salzarulo ............... | A61J 7/0472 235/385 |
| 2010/0100237 A1 | * | 4/2010 | Ratnakar ................ | A61J 7/02 700/232 |

(Continued)

*Primary Examiner* — Brent Swarthout
(74) *Attorney, Agent, or Firm* — Kyle R. Satterthwaite; Ryan W. Dupuis; Ade & Company Inc.

(57) ABSTRACT

A pill bottle or like for medicinal products such as prescription drugs includes an audio device for emitting audible messages to the user of the product, thereby enabling easy identification of the product by the visually impaired. The audio device is incorporated into an internal chamber of a lid of the bottle. The audio device stores data thereon that is received from the computer terminal of a prescription dispensing station, and is configured to wirelessly transmit this data to a separate mobile electronic device, such as a smart phone or tablet computer, which uses the data to cross-check the user's medicinal products for potential interactions and allergen risks, and to create audible reminders for following a prescribed dosage schedule.

6 Claims, 7 Drawing Sheets

(56) References Cited

U.S. PATENT DOCUMENTS

| | | | |
|---|---|---|---|
| 2010/0283601 A1* | 11/2010 | Tai | G06Q 50/24 340/539.12 |
| 2011/0193716 A1* | 8/2011 | Goff | G07G 1/0054 340/686.6 |
| 2013/0110516 A1 | 5/2013 | Abulhaj et al. | |
| 2013/0307683 A1* | 11/2013 | Greenberg | A47G 19/2227 340/539.1 |
| 2014/0081649 A1 | 3/2014 | Langdon et al. | |

* cited by examiner

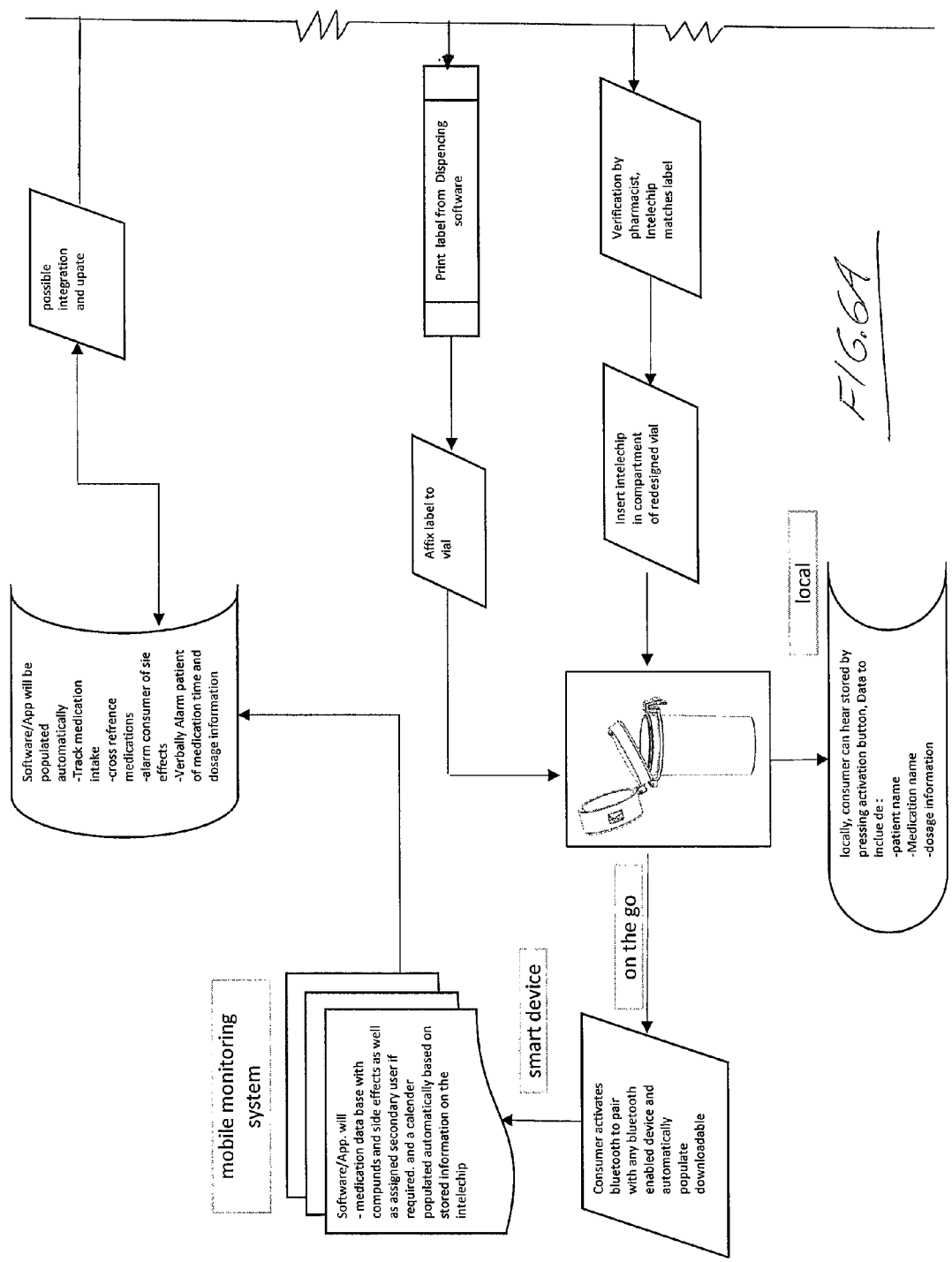

PILL BOTTLE LID INCORPORATING AUDIBLE MESSAGING DEVICE, AND PAIRING THEREOF WITH EXTERNAL DEVICES FOR DOSAGE REMINDER AND CONFLICT CHECKING PURPOSES

CROSS REFERENCE TO RELATED APPLICATIONS

This application claims benefit under 35 U.S.C. 119(e) of Provisional Application Ser. No. 62/010,537, filed Jun. 11, 2014, the entirety of which is incorporated herein by reference.

FIELD OF THE INVENTION

The present invention relates generally to containers and dosage reminders for prescription or non-prescription drugs, and more particularly to such containers which incorporate on-board electronic devices for audible conveyance of information concerning the container contents to visually impaired users and for transfer of content-specific data to external mobile devices that cross-check the container content for potential conflicts and provide audible reminders of scheduled dosage times.

BACKGROUND

In the field of pharmaceutical equipment, it has been previously proposed to outfit prescription drug bottles with means for providing audible messages to visually impaired users who may otherwise struggle to properly identify the particular medication disposed within a given bottle.

U.S. Patent Application Publication 2013/0110516 discloses an audio system that is incorporated at a bottom end of a pill bottle. During a programming step, the audio system receives audio data from a programming unit that uses text-to-speed synthesis to generate audio data based on text data received from a pharmacy computer terminal. However, the placement of the audio system at the bottom of the pill bottle means that the bottle must be lifted up to gain access to an actuation switch on the audio system that triggers the audible message. If a conventional screw-on or snap-on lid of the bottle is not properly seated, or becomes lost or misplaced due to its detachability from the bottle, inversion of the bottle into a position enabling access to the switch could result in spillage of the container contents.

U.S. 2014/0081649 similarly discloses a talking label for a pill bottle that uses a voice-recorded message in one embodiment, and a text-to-speech conversion solution in another. The illustrated embodiments disclose a relatively bulky label attached to the bottle's circumferential wall, while the disclosure also contemplates mounting of the label in an integrally molded pocket of a customized bottle, or configuration of the talking label as a disk-shaped unit incorporated into a recess in the base or lid of the bottle by way of a snap-fit, interference fit or adhesive application. In addition to the already mentioned potential drawbacks of mounting the audible unit at the base of the bottle, mounting the unit to the removable cap of a conventional pill bottle could result in advertent loss of the audible unit in the event the cap is misplaced.

Neither of the forgoing references provide a solution for reminding the user of scheduled dosage times according to the prescribed dosage regime, or for cross-checking potential conflicts with other medications, food or allergies. Additionally, each reference relies on a programming unit separate from the audio unit, thereby requiring purchase of an additional piece of equipment by the pharmacist, and requiring that the audio unit be removed from the bottle and engaged to the matingly configured programming module in order to reprogram the audio unit. Additionally, each reference lacks a rechargeable power source on the audio unit, therefore requiring removal of the audio unit from the bottle for either disposal of the unit or replacement of the battery upon depletion thereof.

In view of the forgoing shortcomings of the prior art, there remains room for improvement.

SUMMARY OF THE INVENTION

According to a first aspect of the invention, there is provided a container assembly having audible message functionality for conveying information concerning contents thereof:

a primary container body having a hollow interior for receipt of the contents therein;

a lid assembly comprising multiple pieces that are collectively movable between a closed position closing off said open upper end of the primary container body and an open position revealing said open upper end of the primary container for access to the hollow interior thereof, and are mated or matable together in a manner cooperating with one another to define an internal chamber delimited by the mated pieces; and an electronic audio device received or receivable within the internal chamber defined by the lid assembly, and operable to emit at least one audible message concerning the contents of the primary container body.

Preferably the multiple pieces of the lid assembly comprise a base engaged to the primary container in the closed position, and a cover mated or matable to the base in a position thereatop to enclose the electronic audio device in a position seated atop the base.

In one embodiment, one of the multiple pieces of the lid assembly is pivotally coupled to the primary container body adjacent the open upper end thereof and pivotal between the open and closed positions.

Preferably a first piece of the lid assembly is pivotally coupled to a first piece of the lid assembly for movement between a locked position mated with and secured to the second piece to enclose the electronic audio device within the internal chamber and a released position withdrawn from the second piece to enable removal and insertion of the audio device.

Preferably the electronic audio device comprises a connection port positioned to align with a cable opening in the lid assembly to enable connection of a cable to the electronic audio device without removal thereof from the internal chamber of the lid assembly.

Preferably the connection port is connected to a charging circuit of the electronic audio device for re-charging a battery of the electronic audio device via the cable.

Preferably the electronic audio device comprises a processor connected to the connection port for receipt of incoming data from the cable by the processor.

Preferably the cable opening is positioned in a circumferential wall of the lid assembly.

Preferably the electronic audio device comprises a message actuator that is operable by way of a cooperating feature of the lid assembly to trigger playback of one or more audible messages concerning the contents of the primary container body.

Preferably the cooperating feature of the lid assembly is an actuator opening therein by which the message actuator of the electronic audio device is accessible.

Preferably the audio device has a plurality of different audibly playable messages stored therein, and at least one message actuator operable to trigger playback of the different audibly playable messages.

Preferably the at least one message actuator consists of a single actuator arranged to playback a respective one of the differently audibly playable messages for each one of plurality of sequential button presses performed on said single actuator.

Preferably the electronic audio device stores data concerning the contents of the primary container body, and comprises a wireless transmitter arranged to transmit said data to an external electronic device.

Preferably, the external electronic device comprises a wireless receiver arranged to receive said data from the electronic audio device and is configured to generate reminders concerning consumption of the contents according to a predetermined dosage schedule, based at least party on said data from the electronic audio device.

Preferably, the data concerning the contents of the primary container body includes a unique identifier for said contents, and the external electronic device is arranged to receive said unique identifier from the audio device and configured to use said unique identifier to cross-check the contents for potential conflicts based on recorded data stored on the external electronic device concerning a user for whom the contents of the container assembly are intended.

The recorded data concerning the user may comprise data on one or more other consumable products that are recorded in the external electronic device as a product of intended or ongoing consumption by said user.

According to a second aspect of the invention, there is provided a container comprising:
a container body having a hollow interior for receipt of the contents therein; and
an on-board electronic device carried on the container body and comprising:
a computer readable medium on which data concerning the contents of the container body is stored;
a wireless transmitter arranged to transmit said data to an external electronic device.

Preferably the data stored on the computer readable medium of the on-board electronic device and transmitted to the external electronic device comprises audio file data, and the on-board electronic device comprises a speaker through which audible messages concerning the contents of the container are conveyed based on the audio file data.

According to a third aspect of the invention, there is provided method of conveying information concerning a consumable substance that is to be dispensed into a container, the method comprising:
at a dispensing station at which the consumable substance is dispensed into the container, receiving data concerning the substance at an on-board electronic device of the container from a computer terminal of the dispensing station, the on-board electronic device being configured to selectively emit audible messages concerning the consumable substance in the container based on the data transmitted to said on-board electronic device;
wirelessly transmitting at least some of the data received by the on-board electronic device of the container to a separate mobile electronic device that is configured to use said data to generate one or more alarms concerning the substance.

Preferably the one or more alarms comprise scheduled reminder alarms concerning consumption of the substance from the container according to a predetermined dosage schedule.

Preferably the one or more alarms comprise conflict alarms concerning potential complications that could result from consumption of the substance based on recorded data concerning a user for whom the contents of the container are intended.

BRIEF DESCRIPTION OF THE DRAWINGS

One embodiment of the invention will now be described in conjunction with the accompanying drawings in which:

FIGS. 6A and 6B are two halves of a schematic flow chart illustrating methods of the present invention, including programming of the pill bottle and use thereof by the prescribed patient in combination with the patient's mobile phone or other smart device for mobile medication reminder functionality.

In the drawings like characters of reference indicate corresponding parts in the different figures.

DETAILED DESCRIPTION

Figure 1:
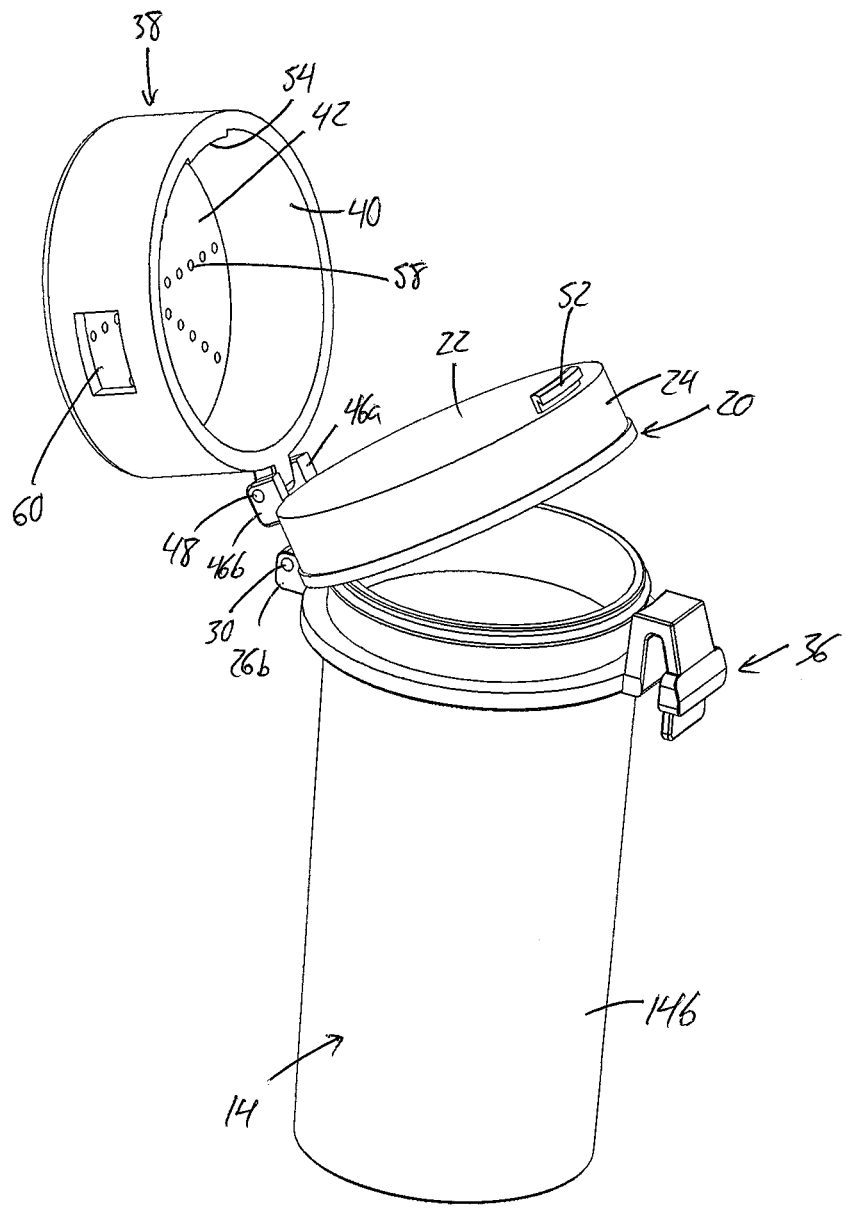
FIG. 1 is a perspective view of a container and two piece lid of a pill bottle according to the present invention with the two-piece lid assembly thereof in a fully opened condition revealing access to both an interior space of the container and an internal chamber of the two-piece lid.

FIG. 1 shows a pill bottle 10 according to one embodiment of the present invention, which has been modified from a conventional pill bottle design in order to provide a unique solution for mounting of an onboard electronic device 12 with audio playback and wireless data transfer capabilities. In a conventional manner, the bottle 10 features a cylindrical container body 14 with a closed lower end and open upper end so as to define a primary storage space of the pill bottle in the form of a hollow cylindrical interior space 16 bound between the circular bottom wall 14a and the cylindrical circumferential wall 14b of the container body 14. This primary storage space accommodates receipt of the product that is to be stored within the bottle, for example a prescribed quantity of pharmaceutical pills prescribed by a doctor and filled by a pharmacist.

The bill bottle departs from a conventional design in the inclusion of a unique two-piece lid assembly 18 hinged to the primary container body 14 near the open upper end thereof. The two-piece lid assembly consists essentially of a base member and a cooperating cover member. The base member 20 features a cylindrical peripheral wall 22 of substantially lesser axial depth than the cylindrical container body 14, and a circular upper panel 24 closing off the top end of the cylindrical peripheral wall 24. The inner diameter of the peripheral wall 22 of the base slightly exceeds the outer diameter of the cylindrical container body 14 so that the cylindrical peripheral wall 22 of the base can fit over the open upper end of the container body 14 so that the upper panel 24 of the base 20 selectively closes off the interior space 16 of the container body 14.

Figure 2:
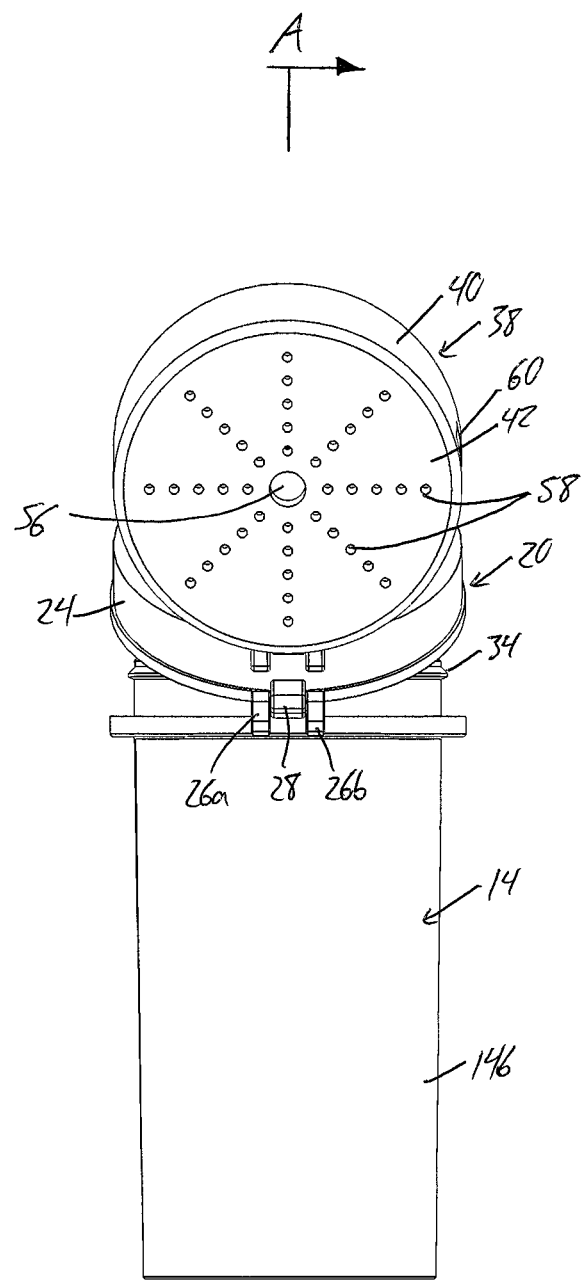
FIG. 2 is a rear elevational view of the pill bottle of FIG. 1.
Figure 3:
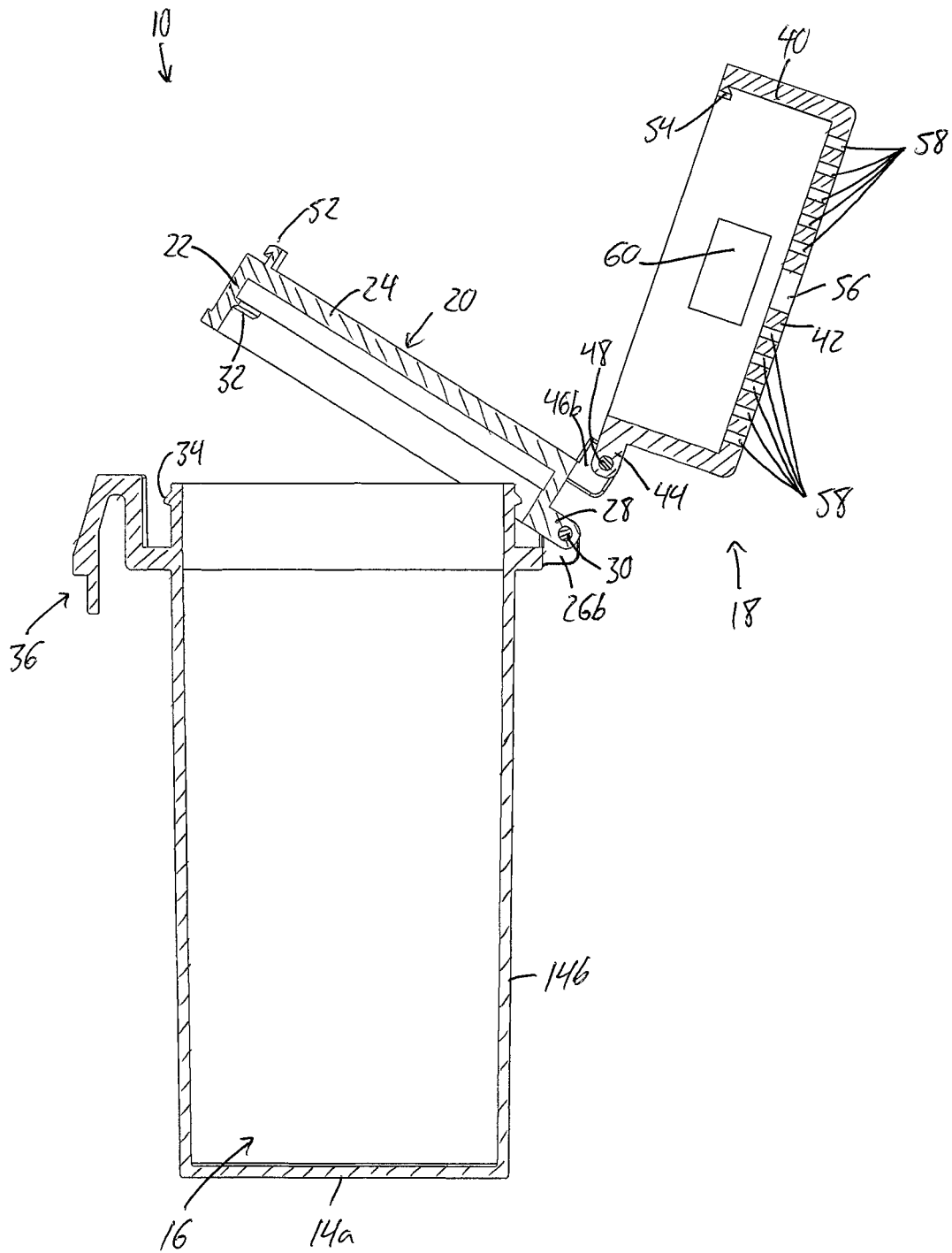
FIG. 3 is a cross-sectional view of the pill bottle of FIG. 2 as seen along line A-A thereof.
Figure 4:
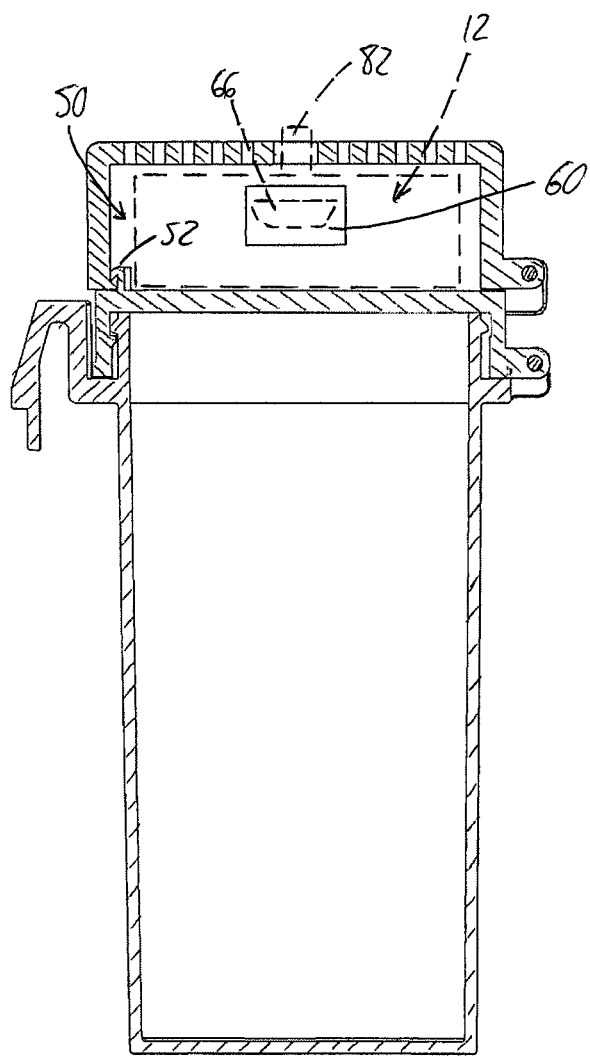
FIG. 4 is a cross-sectional view of the pill bottle in the same viewing plane as FIG. 3, but with the two-piece lid in a fully closed condition topping off the interior of the container and enclosing a schematically illustrated electronic audio device of the pill bottle within the internal chamber of the lid.

The base 22 is pivotally supported on the container body 14 by a pair of lugs 26a, 26b that project outwardly from the container body 14 near the upper end thereof in a common direction. A corresponding tab 28 projects radially outward from the peripheral wall 22 of the base 20 at the bottom end thereof lying opposite the upper panel 24. This tab 28 reaches into the space between the two parallel lugs 26a, 26b of the container body 14 to accept passage of a first pivot pin 30 through the aligned lugs 26a, 26b and tab 28, thereby completing a hinged connection of the base 20 to the container body 14 to allow pivoting of the base into and out of the closed position spanning fully over the open top end of the container body to conceal and obstruct access to the interior space of the container body 14. FIG. 4 shows the base 20 in the closed position, while FIGS. 1 to 3 illustrate the base in an open position withdrawn from over the open top end of the container body to enable access to the interior space 16 thereof during filling of the bottle with prescription pills, and during subsequent retrieval of pills from the bottle by the prescribed user or their caregiver.

The base 20 features a catch tab in the form of a small interior flange 32 projecting inwardly from the peripheral wall 22 at an intermediate location between the top and bottom ends thereof. This interior flange 32 spans a small fractional portion of the circumference of the peripheral wall at a location diametrically opposite to the hinged connection between the base 20 and the container body 14. Near its open upper end, the container body 14 features a small exterior flange 34 projecting radially outward therefrom around the circumference of the container body. The base's interior flange 32 and the container body's small exterior flange 34 are dimensioned to interfere with one another during closing of the base, but are tapered in opposing directions at their distal ends encourage them to slide past one another during this movement rather than causing them to entirely bottom out against one another and prevent closure of the base. Once the interior flange 32 of the base 20 has fully cleared the container body's small exterior flange 34 in the downward direction during closing of the base 20, lifting of the base 20 back into the open position is blocked, until a cooperating release lever 36 on the container body 14 is actuated.

Similar to the base 20, the cover 38 of the two-piece lid assembly 18 features a cylindrical peripheral wall 40, a circular upper panel 42 spanning across the top end of the peripheral wall 40, and a tab 44 projecting radially outward from the lower end of the peripheral wall 40 to form part of a hinged connection between the base and cover. This tab 44 is received between two parallel lugs 46a, 46b that extend outward from the upper end of the base's peripheral wall 22 in the same common direction as the two lugs 26a, 26b on the container body 14. A second pivot pin 48 crosses through the two lugs 46a, 46b and the aligned tab 44 received therebetween, thereby completing a second hinged connection by which the cover 38 can pivot relative to the base 20 about the axis of the second pivot pin 48. While the illustrated embodiment features placement of the two hinges at the same location around the circumference of the container, whereby the pivot axes of the two hinges are parallel, it will be appreciated that the cover need 38 not necessarily be hinged at the same location as the base 20 for movement of the two lid pieces in the same general direction, as the lid and cover could alternatively pivot in different directions.

FIG. 4 shows the cover 38 in a closed condition in which the bottom end of its peripheral wall 40 is seated atop the upper panel 24 of the base, whereby the cover 38 and the base 20 cooperatively delimit a hollow interior chamber 50 surrounded by the cover's peripheral wall 40 at the area between the upper panels 24, 42 of the two lid pieces 20, 38. A second catch tab 52 stands upright from the upper panel 24 of the base 20 at a position around the container that matches that of the first catch tab defined by the interior flange 32. This second catch tab 52 cooperates with a second interior flange 54 defined on the interior of the cover's peripheral wall 40 to secure the cover 38 in the closed condition atop the base. The second catch tab 52 is sharply hooked in shape to actually hook over a pointed top end of the second interior flange 54, whereby they lock together in a positive manner to accomplish a more permanently locked state between the two. Unlike the base of the lid, which must be manually openable and closeable on an ongoing basis by the user of the prescription medication, or they're caregiver, to gain access to the interior space 16 of the container body 14, the internal chamber is not intended for re-opening by the user of the pill bottle.

The upper panel 42 of the cover 38 features a central button-accommodating opening 56, and a plurality of smaller sound holes 58 residing radially outwardly therefrom at positions spread out over the area of the upper panel 42. While the illustrated embodiment shows the smaller holes as arranged in different groups, each consisting of a linear series of holes lying radially of the cover 38 at different angular location around the central opening, the particular layout or pattern of these holes 58 may vary. Finally, a larger cable opening 60 is provided in the peripheral wall 40 of the cover 38 at a select location thereareound. Except for the button-accommodating opening 56, the sound holes 58 and the cable opening 60, the internal chamber of the two-piece lid assembly is otherwise fully enclosed when the cover is in the closed condition.

With reference to FIG. 4, the on-board electronic device, illustrated schematically in broken lines at 12, is housed within the internal chamber 50 of the lid in the fully assembled pill bottle 10, whereby the device 12 is enclosed on all sides thereof. It will be appreciated that the particular means by which the base and cover of the two-piece lid assembly interconnect and lock together, and are optionally attached to the container on a permanent basis to prevent loss, may be varied while accomplishing the same result of an enclosed interior chamber or compartment for housing the on-board electronic device 12. The device 12 features a flat underside seated atop the upper panel 22 of the base 20 in this installed position. With additional reference to FIG. 5, the on-board electronic device features a circular substrate 62 on which the various electronic components of the device are carried. This substrate 62 may define the underside of the overall device that is seated on the base 22 of the lid, or the electronic device may feature an outer housing in which the substrate and the other components of the device are all enclosed.

The on-board device 12 includes a processor, for example embodied in a micro-controller 64 mounted on a printed circuit board (PCB), which may defined the aforementioned substrate. Other components on the same PCB and connected to the processor include a connection port, for example micro-USB port 66 providing both power and data connection terminals; a wireless transceiver, for example a Bluetooth transceiver 68; non-transitory computer readable medium, for example flash memory 70; and an audio-playback device 72 connected to a speaker 74. A rechargeable battery 74 powers the micro-controller 64 and other components via a suitable voltage regulator 76, and is connected to the power terminals of the USB port 66 as part of a recharging circuit for the battery 74. An optional programming interface 78 connected to the micro-controller for programming thereof during product development is shown, but may be omitted in market-ready embodiments. An energy efficient low battery indicator is provided in the form of an light emitting diode (LED) 80, which also be useful for firmware debugging purposes, and may be accompanied by one or more other LEDs useful for such purpose. An on-off push button actuator 82 connected to the micro-controller completes the illustrated embodiment of the on-board electronic device 12.

Turning back to FIG. 4, the USB-port 66 is positioned adjacent an outer periphery of the on-board electronic device 12 for access thereto via the cable opening 60 in the peripheral wall 40 of the lid cover 38 so that a USB cable 84 can be connected to the on-board electronic device after installation thereof in the internal chamber of the lid without requiring removal therefrom. The pushbutton actuator 82 is centered at the top end of the on-board electronic device, whereby a plunger of the pushbutton actuator 82 reaches upwardly through the central opening 56 of the lid cover's upper panel 42, or is at least accessible through this opening 56 for depression of the pushbutton by a thumb or finger of a user.

Having described the structure of the pill bottle, attention is now turned to its preparation for use, and its operation during such use.

Figure 5:
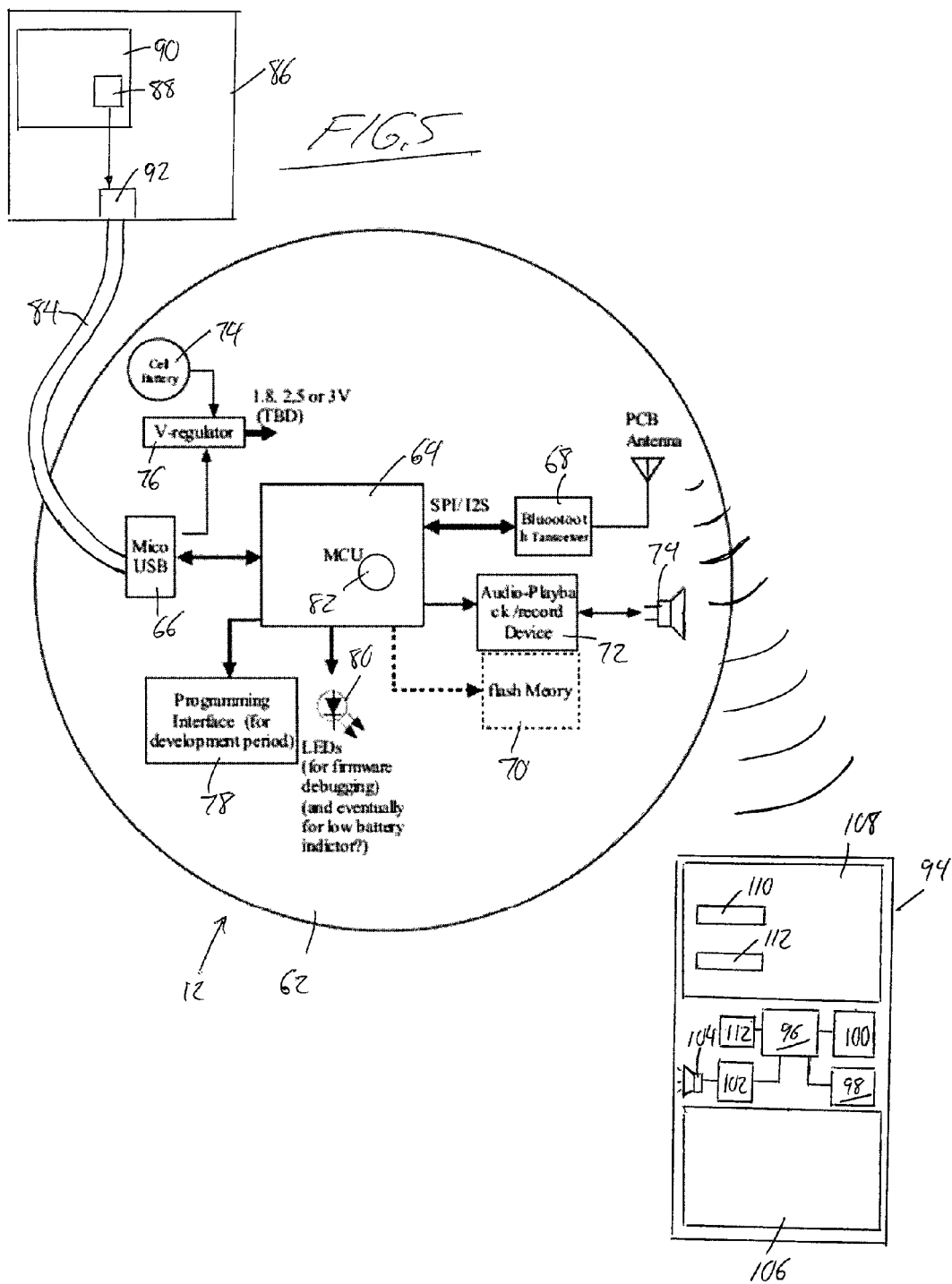
FIG. 5 is a schematic illustration of the electronic audio device of the pill bottle of FIG. 4 during programming thereof by a computer terminal of a pharmacy dispensing station to load the electronic audio device with patient-specific and drug-specific data during filling of a prescription. The figure also demonstrates wireless communication of the electronic audio device with a smart phone, tablet computer or other mobile device in order to convey the drug-specific data thereto for conflict-checking and scheduling purposes.
Figure 6B:
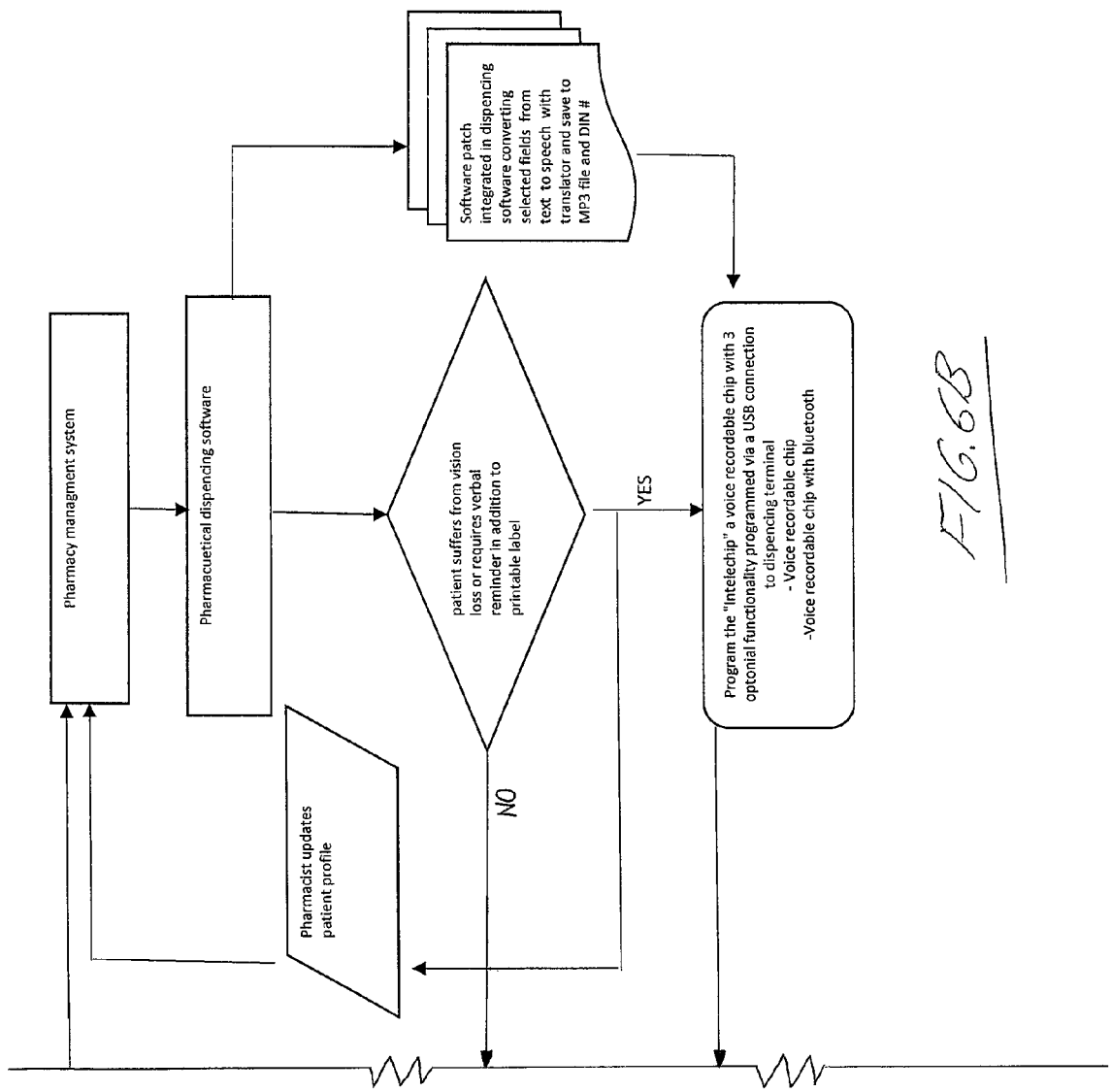

Referring to FIG. 5, when the pill bottle is filled prescription medication at a pharmacy for the first time, a USB cable 84 is used to connect the USB port 66 of the pill bottle's electronic device 12 to a computer terminal 86 at a pharmacy dispensing station for the purpose of programming the electronic device 12 with patient-specific and drug-specific information according to the prescription being filled. Due to the existence of the cable opening 60 in the lid assembly of the pill bottle 10, this can be performed either before or after the electronic device 12 is installed within the internal compartment 50 of the lid assembly. In one embodiment, the pharmacy receives the container and electronic device in a separated unassembled state, and programs the electronic device for the first time prior to installing same within the lid assembly. This way, the programmed electronic device can be checked for proper operation prior to installation thereof into the pill bottle.

A data-capture and conversion software module 88 is installed on the pharmacy terminal 86, or on associated server computer networked thereto, for incorporation into, or interaction with, the pharmacy management software 90 operating on the terminal or associated computer reads data from selected fields of a patient/prescription record of the management software. The data management software and data-capture conversion module 88 comprise statements and instructions stored on non-transitory non-volatile computer readable member connected to the terminal or associated computer for execution by a processor thereof. In one embodiment, the data read from the patient/prescription record by the data capture and conversion module includes 1) the patient name; 2) the medication name and dosage information; and 3) the refill date. The data-capture and conversion software module 80 reads these different categories of data from the patient record, and uses known text-to-speech synthesis techniques to convert the captured text data from these fields into respective audio data files (e.g. wave or MP3 files). Connection of the USB port 66 of the pill bottle's electronic device 12 to the USB port 92 of the pharmacy terminal 86 initiates a programming mode of the electronic device 12, in which the audio files created on the pharmacy terminal 86 are transferred to the pill bottle's electronic device 12 via the USB cable 84 for storage in the non-transitory, and preferably non-volatile, memory 70 thereof. In addition to the text data collected for conversion to audio, the data-capture module 88 also retrieves a drug identification number (or DIN) for the current prescription being filled, which is also transferred to the pill bottle's electronic device 12 via the USB cable 84 for storage in the memory 70 of the electronic device 12.

The micro-controller 64 is pre-programmed by the manufacturer to normally run in a default operating mode (i.e. when not in the programming mode connected to the pharmacy terminal's software module 88 via the USB cable). In the default operating mode, an input of the micro-controller connected to the pushbutton actuator 82 monitors the input for a change in status of the pushbutton between open and closed (i.e. off and on) states, which signals that the pushbutton has been depressed. This button press causes the micro-controller to call on the audio-playback device 72 to playback one of the audio files stored in memory 70, and also increments a counter function of the micro-controller by one. In the present embodiment, in which there are three audio files containing different categories of prescription information (patient name, medication name and dosage information, and refill date), the micro-controller resets the counter-function to an initial value after three button presses. Each one of the three possible values of the counter corresponds to a respective one of the three different audio files. Each time of the pushbutton is pressed, the current value of the counter determines which one of the audio files is played back as an audible message through the speaker 74. In the present embodiment, a first button press plays back the patient name, a second button press plays back the medication name and dosage information, and a third button press plays back the refill date.

The number of different playable messages and the prescribed order in which the different audible messages are played may of course be varied within the scope of the present invention. Examples of dosage information include the dosage frequency, e.g. 'twice daily'; the dosage amount, which may be related to the pill strength, e.g. '500 mg'; and any other information pertinent to consumption or administration of the medication, e.g. 'take with food'.

Once the pill bottle's electronic device 12 has been loaded with the audio data during the programming stage, the electronic device 12 switches to its default operation mode, and the pharmacist filling the prescription performs three button pushes in order to hear the three audible messages and confirm that the electronic device 12 has been properly programmed with the correct prescription information. With the USB cable disconnected, the electronic device 12 is placed inside the cover 38 of the lid assembly 18, and the cover and base 20 are closed together to secure the electronic 12 within the locked internal compartment 50 of the lid assembly 18. With the appropriate type and quantity of medication dispensed into the container body 14 of the pill bottle 10, the locked together base and cover of the lid assembly 18 are closed onto the container body to secure the medicinal contents therein.

The bill bottle and the prescription therein are sold to the customer e.g. the prescribed patient, or authorized purchaser acting on behalf thereof). At anytime, the user of the pill bottle (e.g. the patient, or their caregiver) can depress the push button one or more times to confirm that they are in possession of the correct pill bottle for the medication they are intending to consume or dispense. The audible messages are especially helpful for those with visual impairment who are unable to see or accurately read conventional printed labels. Nonetheless, the container body 14 may be equipped with conventional printed labels, which can still prove valuable, for example in the event that the battery of the on-board electronic device becomes depleted or the device is otherwise rendered inoperative by physical damage or other cause. The battery 74 of the on-board electronic 12 can be charged at any time by connecting the USB port 66 to the powered USB port of a desktop laptop or tablet computer or other USB equipped device using a suitable USB cable mated to the pill bottle's onboard electronic device 12 device through the cable opening 60 of the lid assembly. All or part of the lid assembly 18, for example at least the cover 38 thereof, may be transparent or translucent to allow visual detection of the low battery LED 80 by patients with sufficient visual acuity. Alternatively or additionally, the device 12 may feature an audible low-battery alarm, whether a spoken audible message like those employed for the prescription information, or a generic alarm sound (e.g. an intermittent or continual beep).

In the normal mode of operation of the electronic device 12, in addition to monitoring for a brief momentary button depression that triggers the audible prescription messages, the micro-controller is also programmed to detect a different type of input from the pushbutton 82, for example a held down state of the pushbutton exceeding a certain threshold of time, e.g. 3-seconds. This signal switches the device over to a communication mode of operation, in which the Bluetooth transceiver 68 searches for and pairs with Bluetooth compatible smart devices, for example mobile electronic devices such as smart phones, tablet computers, laptop computers, etc. One such smart device 94 is schematically shown in FIG. 5, and features a processor 96, non-transitory non-volatile computer readable memory 98 connected to the processor, a wireless transceiver 100 connected to the processor 96 and of a type compatible with the transceiver of the pill bottle's mobile smart device (e.g. Bluetooth transceiver), an audio-playback device 102, a speaker 104 connected thereto, and software stored in the computer readable memory 98 in the form of statements and instructions for execution by the processor. The stored software includes a prescription management software application for functional cooperation with the on-board electronic device 12 of the pill bottle 10. As an alternative to Bluetooth, the pill bottle electronic device 12 and smart device 94 may employ other types of wireless communication, and for example use near field communication (NFC) transceivers in these devices to data therebetween.

When the mobile smart device 94 running the prescription management software application wirelessly pairs with the on-board electronic device 12 of the pill bottle 10, the on-board electronic device 12 transmits the DIN and at least one of the audio files to the mobile smart device 94, where they are stored in the computer readable memory 98. When the prescription management software application of the mobile smart device has received different DIN numbers from the on-board electronic devices of different pill bottles, it uses the DIN numbers to cross-check the medications represented thereby for known interactions that can be potentially harmful to the patient, or an effect on the efficacy the medication. Additionally, a user-interface of the mobile device software application may include tools for users to manually or verbally enter other relevant information not received from a pill bottle of the present information. For example, this may include identification of non-prescription medications taken by the patient, prescription medications dispensed in a conventional container with no on-board electronic device capable of transmitting the DIN, types of foods consumed by the user, and/or known allergies of the user. This information may be manually entered through a combination of an onscreen or tactile keyboard input 106 of the mobile device 94 and a display screen 108 thereof in which an on-screen user-interface is presented by the execution of the software app and includes one or more user-fillable fields 110 or user-selectable options for entering drug, food and/or allergy information. Alternatively, the food/drug/allergy information may be entered verbally through a microphone 112 of the mobile device 94 using known voice recognition techniques. The user entered information is used along with any received DIN numbers to check for potential interactions or conflicts.

Existing databases for cross-checking prescription drugs against other drugs, foods and allergies are available for such purposes, for example including those available from PEPID (http://www.pepid.com). The one or more databases may be downloaded to the mobile electronic device 94, for example during installation of the software application or a subsequent update thereof, for local storage in the memory 98 of the mobile device 94, or may be hosted by a separate server that is remotely accessed by the mobile device 94 over the internet or another communication network. In the event that the cross-check reveals a conflict, such as a potential interaction between two drugs, a potential interaction between a drug and a food, or a presence of an allergen in the medication that conflicts with the user's allergies, a conflict alarm is activated to warn the user of this conflict. The alarm may include audible notification emitted from the speaker 104 of the mobile device, and/or visual notifications presented on the display screen 108 thereof.

The user interface of the prescription management software application includes an input option for receiving a prescribed or preferred time of day at which the medication in the pill bottle 10 is to be taken (or multiple times, in the event of a medication that is to be taken multiple times daily). The input option may be presented as an on screen field or tool 112 operable through keyboard, touchscreen or other input of the device 94, For example, the software may be configured to automatically prompt the user for this prescribed or preferred dosage time in response to pairing of the mobile device with the on-board electronic device of the pill bottle and receipt of the DIN and audible messages therefrom. Using the inputted time(s), a scheduling function of the software application generates scheduled reminder alarms that will automatically play one or more audio files that were received by the mobile device from the pill bottle via the playback device 102 and connected speaker 104. In the present embodiment, the mobile device receives at least the audio file with the medication name, whereby the audible message emitted from the speaker 104 as a reminder to patient explicitly identifies the specific medication to be taken at that time.

When the contents of the pill bottle are fully consumed, the pill bottle is returned to the pharmacy, where the pill bottle can be re-used for the same patient and prescription without reprogramming, or can be re-used for dispensing a different prescription to the same patient or a different patient, in which case the on-board electronic device can be reprogrammed with new prescription-specific information without removal from the lid assembly by connecting the USB cable from the pharmacy computer terminal 86 through the cable opening 60 in the lid assembly.

While the detailed embodiments above are presented in the context of prescription medications dispensed by a pharmacist, it will be appreciated that the electronic audio device 12 may likewise be used to enable audible identification of bottle contents for over-the-counter medications, and to enable pairing with a mobile electronic device for allergen and interaction cross-checking and/or dosage reminder purposes. While the detailed embodiments are described in reference to a cylindrical pill bottle, it will be appreciate that containers of various shapes and medicinal products of various forms (e.g. liquid) would also be compatible with inventive aspects of the unique embodiments disclosed herein.

While the illustrated embodiment has the two piece lid assembly permanently hinged to the container body to prevent the same from being lost or misplaced, other embodiments employing a more conventional screw-on or snap-on fit between the base of the lid assembly and the container body would still have such beneficial features as the concealed and protected enclosure of the on-board electronic device in the internal compartment of the multi-piece lid assembly, the accessibility of the on-board electronic device for recharging and reprogramming without removal from the lid assembly, wireless communication with external smart devices for conflict checking and/or scheduling purposes.

Since various modifications can be made in my invention as herein above described, and many apparently widely different embodiments of same made within the scope of the claims without departure from such scope, it is intended that all matter contained in the accompanying specification shall be interpreted as illustrative only and not in a limiting sense.

The invention claimed is:

1. A system for cross-checking medicinal or other consumable products for potential conflicts, said system comprising:
  a plurality of containers for a given user, each of said containers containing a different respective consumable product therein and each comprising:
    a container body having a hollow interior in which the respective consumable product is received; and
    an on-board electronic device carried on the container body and comprising:
      a non-transitory computer readable medium on which data concerning the respective consumable product of the container body is stored, said data comprising a unique identifier for said respective consumable product;
      a wireless transmitter arranged to transmit said data;
  an external electronic device that comprises a wireless receiver for receiving said data from the audio device of each of said plurality of containers, and is configured to (a) receive a collection of multiple unique identifiers from said given user's plurality of containers, (b) specifically cross-check said multiple unique identifiers against one another for potential conflicts between the different consumable products represented thereby, and (c) generate an alarm and present said alarm to the given user upon detection of a conflict specifically between said different consumable products represented by the multiple unique identifiers received from said given user's plurality of containers.

2. The system of claim 1 wherein the external electronic device is a mobile electronic device.

3. The system of claim 1 wherein the external electronic device is an electronic device of the patient's.

4. The system of claim 1 wherein the external electronic device is a mobile electronic device of the patient's.

5. The system of claim 1 wherein the on board electronic device and the external mobile electronic device are arranged to communicate said data via Bluetooth.

6. The system of claim 1 wherein the on board electronic device and the external mobile electronic device are arranged to communicate said data by near field communication.

* * * * *